(12) United States Patent
Lee

(10) Patent No.: US 8,608,711 B2
(45) Date of Patent: Dec. 17, 2013

(54) INFUSION PORT

(75) Inventor: Im-Suk Lee, Yongin-si (KR)

(73) Assignee: Medipharma Plan Co., Ltd., Anseong-Si (KR)

(*) Notice: Subject to any disclaimer, the term of this patent is extended or adjusted under 35 U.S.C. 154(b) by 0 days.

(21) Appl. No.: 13/129,614

(22) PCT Filed: Oct. 9, 2009

(86) PCT No.: PCT/KR2009/005777
§ 371 (c)(1),
(2), (4) Date: May 17, 2011

(87) PCT Pub. No.: WO2011/021742
PCT Pub. Date: Feb. 24, 2011

(65) Prior Publication Data
US 2012/0136321 A1    May 31, 2012

(30) Foreign Application Priority Data
Aug. 17, 2009  (KR) ................ 10-2009-0075803

(51) Int. Cl.
*A61M 5/31*    (2006.01)
(52) U.S. Cl.
USPC .......... 604/249; 604/251; 604/256; 604/257; 604/537; 604/411; 604/414
(58) Field of Classification Search
USPC ......... 604/87, 88, 89, 91, 244, 246, 247, 249, 604/251, 255, 256, 257, 262, 537, 539, 604/288.01, 288.02, 288.03, 403, 408, 411, 604/414, 415
See application file for complete search history.

(56) References Cited

U.S. PATENT DOCUMENTS 4,676,775 A * 6/1987 Zolnierczyk et al. ........... 604/28
6,685,692 B2 * 2/2004 Fathallah ..................... 604/411

FOREIGN PATENT DOCUMENTS

| KR | 10-2009-0028974 | 3/2009 |
|---|---|---|
| KR | 10-0903740 | 6/2009 |
| KR | 20-2009-0007179 | 7/2009 |

* cited by examiner

*Primary Examiner* — Bhisma Mehta
(74) *Attorney, Agent, or Firm* — Lexyoume IP Meister, PLLC.

(57) ABSTRACT

Disclosed is an infusion port for regulating the inflow of an aqueous solution of an aqueous-solution pack into an external ringer spike as at least part of the ringer spike is inserted or withdrawn. The infusion port comprises an inflow part, a securing part, and a cover part. The inflow part is formed with at least one first inflow hole into which the ringer spike is inserted, so as to allow the inflow of the aqueous solution of the aqueous-solution pack as the ringer spike is inserted. Consequently, as the first inflow hole of the inflow part moves outside or inside the securing part, it is possible to regulate the flow of the aqueous solution of the aqueous-solution pack through the first inflow hole and into the ringer spike disposed inside the inflow part.

8 Claims, 4 Drawing Sheets

INFUSION PORT

TECHNICAL FIELD

The present invention relates to an infusion port, and more particularly, to such an infusion port that is configured to be engaged with an inlet port of an aqueous-solution pack so that a patient can be administered with a drug solution contained in the aqueous-solution pack.

BACKGROUND ART

In general, an aqueous solution such as nutritional supplement, distilled water, and the like, including physiological salt solution and glucose is stored in an aqueous-solution pack having a certain shape in hospitals, etc., where a medical treatment or a surgical operation is performed on a patient. In addition, the infusion port is engaged with an inlet port connected to a lower end of the aqueous-solution pack, and a ringer spike is inserted into a sealing cap disposed at a lower end of the infusion port in order to supply the aqueous solution to the patient so that the aqueous solution can be administered to the patient. A conventional infusion port entails a problem in that the sealing cap is formed of a rubber material, which contributes to an increase in the overall expense incurred to manufacture the infusion port due to a high unit price. Moreover, when the ringer spike is inserted into the sealing cap, it is torn to create rubber fragments, which may be in turn introduced into the infusion port. Thus, since noxious substances harmful to the human body are produced from the rubber fragments of the sealing cap, they may be mixed with the aqueous solution. Further, the noxious substances mixed with the aqueous solution may be administered to the patient due to leakage of an additive added to the sealing cap during the manufacture of the sealing cap of a rubber material, leading to a serious deterioration in safety of the patient.

DISCLOSURE OF INVENTION

Technical Problem

Accordingly, the present invention has been made to solve the above-mentioned problem associated with the prior art, and it is an object of the present invention to provide an infusion port which can prevent foreign substances, additives and the like from leaking and being introduced into the infusion port by eliminating the necessity of use of the sealing cap of a rubber material, and can be used in a medical application such as an aqueous solution pack, a blood bag, and the like in which the manufacturing cost can be saved.

Technical Solution

To achieve the above objects, in one aspect, the present invention provides an infusion port regulating the inflow of an aqueous solution of an aqueous-solution pack into an external ringer spike as at least part of the ringer spike is inserted into or withdrawn from the infusion port, the infusion port comprising: an inflow unit configured to allow the ringer spike to be inserted thereto and having at least one first inflow hole formed thereon so as to allow for the inflow of the aqueous solution of the aqueous-solution pack as the ringer spike is inserted into the infusion port; a securing unit configured to surround at least part of the inflow unit and having a movement hole formed at one end thereof such that the first inflow hole of the inflow unit is moved to the outside or the inside of the securing unit as the ringer spike is inserted into or withdrawn from the infusion port, and configured to secure the inflow unit when the first inflow hole is moved to the outside of the securing unit; and a cover unit configured to house the securing part therein and having a second inflow hole formed at one end so as to allow for the inflow of the aqueous solution into the cover unit through the second inflow hole upon the partial insertion of the cover unit into an inlet port disposed at the aqueous-solution pack.

Preferably, the infusion port may further include a securing cap configured to be engaged to the cover unit so that it secures the inflow unit upon the withdrawal of the ringer spike from the infusion port, and having a central hole formed on one side thereof so as to allow for the insertion and withdrawal of the ringer spike into and from the securing cap through the central hole. In addition, the infusion port may further include a contamination preventive cap configured to be engaged to the securing cap so as to prevent the central hole of the securing cap from being exposed to the outside.

Preferably, the securing cap may further include a barrier membrane configured to cover the central hole of the securing cap and formed of a flexible material to allow for the insertion and withdrawal of the ringer spike into and from the securing cap through the barrier membrane.

In addition, preferably, the securing cap may further include a retaining protrusion formed along the circumference of the central hole thereof, and the securing unit may further include a first retaining step formed at a lower end thereof so as to be engaged with the retaining protrusion of the securing cap. In addition, the cover unit may further include a second retaining step formed at a lower end thereof so as to be engaged with the first retaining step of the securing unit.

In one embodiment of the present invention, at least one of the securing unit and the inflow unit may further include a stepped part formed thereon so as to allow the securing unit to secure the inflow unit upon the insertion of the ringer spike thereto.

In another embodiment of the present invention, at least one of the securing unit and the inflow unit may further include a first inclined part formed thereon so as to allow the securing unit to secure the inflow unit upon the insertion of the ringer spike thereto.

In the meantime, the inflow unit may have a predetermined coefficient of elasticity to allow the ringer spike to be firmly inserted into the inflow unit upon the insertion of the at least part of the ringer spike thereto.

Advantageous Effects

According to the infusion port of the present invention, the inflow unit can be moved through the movement hole of the securing unit. Thus, when the inflow unit is moved to the outside of the securing unit to cause the first inflow hole of the inflow unit to be exposed to the outside of the securing unit, the aqueous solution contained in the aqueous-solution pack flows into the inflow unit through the first inflow hole so that it can be administered to a body of a patient through the ringer spike.

In addition, when the inflow unit is moved to the inside of the securing unit to cause the first inflow hole of the inflow unit to enter the securing unit, the aqueous solution contained in the aqueous-solution pack is prevented from flowing into the inflow unit through the first inflow hole. Thus, when the ringer spike is separated from the inflow unit, the aqueous solution contained in the aqueous-solution pack can be prevented from flowing to the outside of the infusion port.

BRIEF DESCRIPTION OF THE DRAWINGS

The above and other objects, features and advantages of the present invention will be more clearly understood from the following detailed description taken in conjunction with the accompanying drawing, in which.

Figure 1:
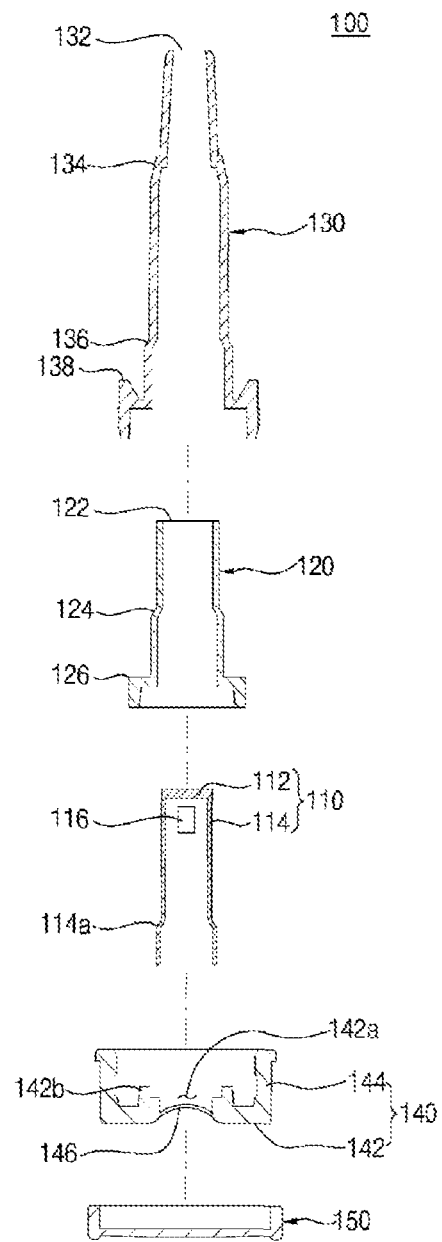
FIG. 1 is an exploded cross-sectional view illustrating an infusion port according to one embodiment of the present invention.

| [Explanation on symbols] | |
|---|---|
| 100: | infusion port |
| 110: | inflow unit |
| 120: | securing unit |
| 130: | cover unit |
| 140: | securing cap |
| 150: | contamination preventive cap |
| 200: | aqueous-solution pack |
| 300: | ringer spike |

BEST MODE FOR CARRYING OUT THE INVENTION

A preferred embodiment of the present invention will be described hereinafter in detail with reference to the accompanying drawings.

The present invention can be variously modified in various embodiments and specific embodiments will be described and shown in the drawings. The invention is not limited to the embodiments, but it should be understood that the invention includes all the modifications, equivalents, and replacements belonging to the spirit and the technical scope of the invention.

Terms, "first", "second", and the like, can be used to describe various elements, but the elements are not limited to the terms. The terms are used only to distinguish one element from another element. For example, a first element can be designated by a second element without departing from the scope of the invention. Similarly, a second element can also be designated by a first element.

The terminology herein is merely used to describe specific embodiments of the present invention, but is not intended to limit the present invention. It should be noted that, in this specification and the appended claims, the singular forms, "a," "an," or "the", includes plural referents unless the context clearly dictates otherwise. It should be appreciated that the terms "comprise(s)", "comprising", "include(s)", and "including", or "have(has)" when used in this specification and in the following claims are intended to specify the presence of stated features, integers, steps, acts, elements, components or combination thereof, but they do not preclude the presence or addition of one or more other features, integers, steps, acts, elements, components or combination thereof.

Unless defined otherwise, all technical and scientific terms used herein have the same meaning as commonly understood by one of ordinary skill in the art to which this invention belongs.

The terms same as ones defined in a commonly-used dictionary should be interpreted as including the meaning in accordance with the meaning in the context of the related art, and should not be interpreted as being ideally or excessively literally unless they are defined clearly in this specification.

Now, the preferred embodiments of the present invention will be described hereinafter in more detail with reference to the accompanying drawings.

Figure 2:
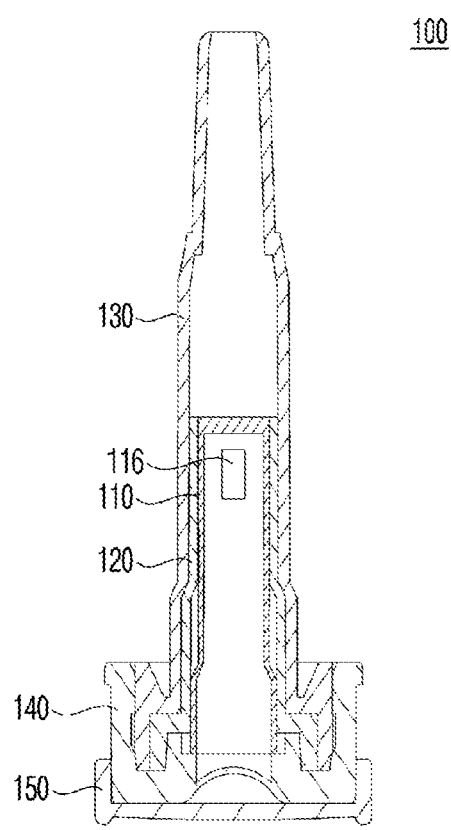
FIG. 2 is a cross-sectional view illustrating an assembled state of the infusion port of FIG. 1.
Figure 3:
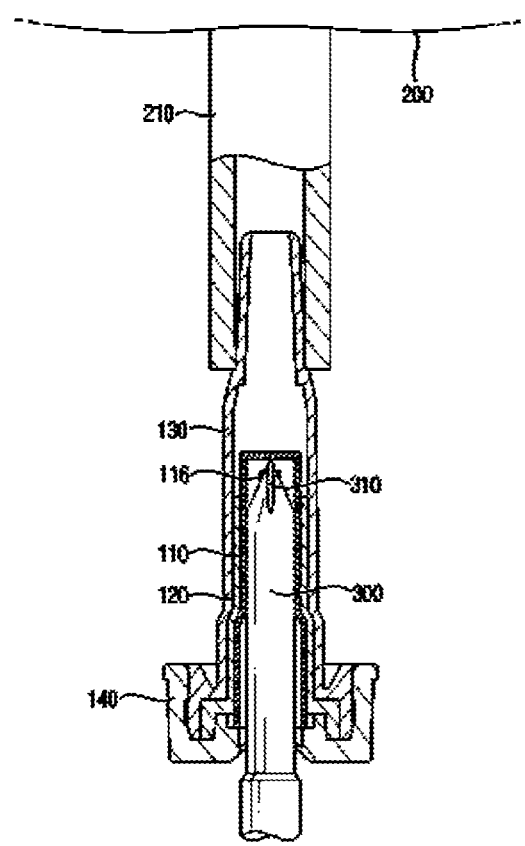
FIG. 3 is a cross-sectional view illustrating an engagement state of an infusion port according to one embodiment of the present invention, a ringer spike, and an aqueous-solution pack.

FIG. 1 is an exploded cross-sectional view illustrating an infusion port according to one embodiment of the present invention, FIG. 2 is a cross-sectional view illustrating an assembled state of the infusion port of FIG. 1, and FIG. 3 is a cross-sectional view illustrating an engagement state of an infusion port according to one embodiment of the present invention, a ringer spike, and an aqueous-solution pack.

Referring to FIGS. 1 and 2, an infusion port 100 according to this embodiment includes an inflow unit 110, a securing unit 120, a cover unit 130, a securing cap 140, and a contamination preventive cap 150.

The inflow unit 110 allows at least part of an external ringer spike 300, i.e., an upper portion of the ringer spike 300 to be inserted thereto. The inflow unit 110 includes a top surface 112 formed a circular shape and a first side surface 114 extending in the longitudinal direction thereof. The upper portion of the ringer spike 300 is inserted to the inside of the first side surface 114.

The inflow unit 110 can have a predetermined coefficient of elasticity to allow the upper portion of the ringer spike 300 to be firmly inserted into the inflow unit 110 upon the insertion of the upper portion of the ringer spike 300 thereto. For example, the inflow unit 110 may be formed of a polypropylene material having the predetermined coefficient of elasticity so that the upper portion of the ringer spike 300 can be inserted into the inflow unit 110. In addition, the inflow unit may include a first stepped part, i.e., a first movement-preventing step 114a formed at a lower portion of the first side surface 114 thereof in such a fashion as to be constructed in a stepped manner along the outer circumference of the first side surface 114.

Further, the inflow unit 110 includes at least one first inflow hole 116 formed at an upper portion of the sidewall 114 contacting with the top surface 112 on the outer surface, i.e., the first side surface 114 of the inflow unit 110. The first inflow hole 116 is formed symmetrically based on the center of the inflow unit 110 as shown in FIGS. 1 and 2, and can have a quadrangular shape. Alternatively, the first inflow hole 116 may have a circular or polygonal shape, and may be formed in asymmetrically based on the center of the inflow unit 110

The securing unit 120 is formed to surround the first side surface 114 of the inflow unit 110, and has a movement hole 122 formed at a top end of the securing unit 120. The first inflow hole 116 of the inflow unit 110 is moved to the outside or the inside of the securing unit 120 as the ringer spike is inserted into or withdrawn from the infusion port.

When the upper portion of the ringer spike 300 is inserted into the inflow unit 110 accommodated in the securing unit 120, the top surface 112 and the upper portion of the first side surface are moved to the outside of the securing unit 120 through the movement hole 122 along the movement direction of the ringer spike 300. On the other hand, when the upper portion of the ringer spike 300 is withdrawn from the inflow unit 110, the top surface 112 and the upper portion of the first side surface 114 are moved to the inside of the securing unit 120 through the movement hole 122 along the movement direction of the ringer spike 300. At this time, the upper portion of the first side surface 114 is preferably moved to the outside of the securing unit 120 in an exposed manner.

The securing unit 120 can include a second movement-preventing step 124 formed along the outer circumferential surface thereof. When the inflow unit 110 is exposedly moved to the outside of the securing unit 120 through the movement hole 112, the first movement-preventing step 114a is retained by the second movement-preventing step 124 so that the inflow unit 110 can be fixed, but not exposed to the outside of the securing unit 120 in its entirety Besides, the securing unit 120 can include a second stepped part, i.e., a first retaining step 126 formed at a bottom thereof to be opposed to the top thereof in such a fashion as to be constructed in a stepped manner along the outer circumference of the bottom thereof. The first retaining step 126 is formed to be larger than the securing unit 120, and can be formed as a "⌐" shaped protrusion so as to be engaged with the securing cap 140, which will be described later.

Although not shown, the first retaining step 126 may be formed as a "⊏" shaped protrusion to surround the lower end of the inflow unit 110 so that when the ringer spike 300 is withdrawn from the inflow unit 110, the inflow unit 110 can be fixedly retained at the lower end thereof by the first retaining step 126, but not moved in the movement direction of the ringer spike 300.

The cover unit 130 houses the securing unit 120 therein, and is partly inserted into an inlet port 210 disposed at the bottom of the aqueous-solution pack 200.

The cover unit 130 may be formed in a tapered shape that is gradually reduced in diameter as it goes toward the bottom from the top thereof so as to be firmly inserted into the inlet port 210. A part of the cover unit 130 inserted into the inlet port 210 is defined as an upper portion of the cover unit 130, and a part opposed to the upper portion of the cover unit 130 is defined as a lower portion of the cover unit 130.

The cover unit 130 includes a second inflow hole 132 formed at the top end thereof so as to allow for the inflow of the aqueous solution into the cover unit 130 through the second inflow hole. In addition, the cover unit 130 may include a third movement-preventing step 134 formed on the outer circumference of the upper portion thereof. When the upper portion of the cover unit 130 is inserted into the inlet port 210, a bottom of the inlet port 210 is retained by the third movement-preventing step 134 so that the cover unit 130 can be firmly inserted and secured into the inlet port 210.

The cover unit 130 may include a fourth movement-preventing step 136 formed on the outer circumference of the lower portion thereof so as to correspond to the second movement-preventing step 124 of the securing unit 120 when the securing unit 120 is accommodated in the cover unit 130. When securing unit 120 is accommodated in the cover unit 130, the second movement-preventing step 124 of the securing unit 120 is retained by the fourth movement-preventing step 136 so that the securing unit can be prevented from escaping to the outside and the securing unit 120 can be stably secured to the inside of the cover unit 130.

In addition, the cover unit 130 may include a second retaining step 138 formed at a bottom thereof so as to correspond to the first retaining step 126 of the securing unit 120. The second retaining step 138 can be engaged with the first retaining step 126 along the outer circumferential surface of the first retaining step 126 in a concavo-convex relation. In addition, the outer circumferential surface of the second retaining step 138 is brought into close contact with the inner circumferential surface of the securing cap 140 so that the cover unit 130 can be engaged with the securing cap 140.

Meanwhile, the inlet port 210 is formed as a flue that is opened at a top and a bottom thereof. The aqueous solution can be injected into the top of the inlet port 210 and can be introduced into the cover unit 130 through the second inflow hole 132 of the cover unit 130.

The securing cap 140 is engaged with the cover unit 130 so that when the ringer spike 300 is withdrawn from the inflow unit 110, the securing cap 140 secures the inflow unit 110 which is moved together with the ringer spike 300 in the movement direction of the ringer spike 300 so as to prevent the inflow unit 110 from escaping to the outside of the infusion port 100.

In this embodiment, the securing cap 140 includes a bottom surface 142 that is formed in a circular shape and a second side surface 144 that is formed so as to surround the outer surface of the second retaining step 138.

The securing cap 140 includes a central hole 142a formed at the center of the bottom surface 142 thereof so as to allow for the insertion and withdrawal of the ringer spike 300 into and from the securing cap through the central hole. In addition, the securing cap 140 includes a retaining protrusion 142b formed in a "⌊" shape along the circumference of the central hole 142a thereof in such a fashion as to be spaced apart from the central hole 142a by a predetermined interval. The outer circumferential surface of the retaining step 142a is brought into close contact with the inner circumferential surface of the first retaining step 126 of the securing unit 120 so that the securing cap 140 can be engaged with the securing unit 120 in a concavo-convex relation. Besides, a lower end of the inflow unit 110 can be brought into close contact with a top surface of the retaining protrusion 142b.

In the meantime, a top of the bottom surface 142 is brought into close contact with a lower end of the securing unit 120 and a lower end of the cover unit 130, and the bottom surface 142 can be brought into close contact with the contamination preventive cap, which will be described later.

The second side surface 144 surrounds the outer circumferential surface of the second retaining step 138 to secure the second retaining step 138. The first retaining step 126 and the second retaining step 138 are engaged with each other in a concavo-convex relation between the second side surface 144 and the retaining protrusion 142b so that the securing cap 140 can secure the cover unit 130 and the securing unit 120.

The securing cap 140 is formed to cover the central hole 142a, and further include a barrier membrane 146 formed of a flexible material to allow for the insertion and withdrawal of the ringer spike 300 into and from the securing cap through the barrier membrane.

The barrier membrane 146 can be formed to cover the central hole 142a so a to prevent the foreign substances from being introduced into the inflow unit 110, the securing unit, and the cover unit 130 through the central hole 142a prior to the use of the infusion port 100. In addition, since the ring spike 300 is required to pierce the barrier membrane 146 in order to use the infusion port 100, the barrier membrane 146 can be used for the purpose of confirming whether the infusion port 100 has been used and preventing the re-use of the infusion port 100.

The contamination preventive cap 150 is formed to surround the bottom surface 142 and a part of the second side surface 144 of the securing cap 140 so as to be engaged with the securing cap 140. The contamination preventive cap 150 can serve to cover the central hole 142a and the barrier membrane 146 of the bottom surface 142 so as to prevent the central hole 142a and the barrier membrane 146 from being exposed to the outside and contaminated. In addition, the contamination preventive cap 150 can be removed from the securing cap 140 and can be discarded to insert the ringer spike 300 into the securing cap 140 when the infusion port is used.

Further, the contamination preventive cap 150 may be formed in various manners such as an easy film, a flip-off type, and the like.

Hereinafter, the operation and effects of the present invention in which the infusion port 100 and the ringer spike 300 are engaged with each other will be described with reference to FIG. 3.

Referring to FIG. 3, the contamination preventive cap 150 is removed from the securing cap 140, and then the bottom surface 142 and the barrier membrane 146 are sterilized by being rubbed with alcohol-impregnated cotton in order to administer the aqueous solution of the aqueous-solution pack 200 to a patient. Then, when a top of the ringer spike 300 is inserted into the inflow unit 110 while piecing the barrier membrane 146, it is brought into close contact with a top surface 112 of the inflow unit 110. Thereafter, an advancing force of the ringer spike 300 acts in the direction of the aqueous-solution pack 200 to cause the inflow unit 110 to be exposedly moved to the outside of the securing unit 120 through the movement hole 122 of the securing unit 120 so that the first inflow hole 116 of the inflow unit 110 is exposed to the inside of the cover unit 130.

Then, the aqueous solution contained in the aqueous-solution pack 200 is introduced into the cover unit 130 through the second inflow hole 132 of the cover unit 130 via the inlet port 210, and then flows into the first inflow hole 116 exposed to the inside of the cover unit 130. Thereafter, the aqueous solution flowing into the inflow unit 110 through the first inflow hole 116 is introduced into an aqueous solution-introducing hole 310 formed at a top of the ringer spike 300, and then is administered to the patient through a tube connected to a bottom of the ringer spike 300.

In this case, the ringer spike 300 is required to be firmly inserted into the inflow unit 110 so as to prevent the aqueous solution of the aqueous-solution pack 200 from being leaked to an empty space which may be created between the inflow unit 110 and the ringer spike 300.

Thereafter, the ringer spike 300 is moved in the direction opposite to the aqueous-solution pack 200 in order to withdraw the ringer spike 300 out of the infusion port 100 after completion of the administration of the aqueous solution of the aqueous-solution pack 200 to the patient. Then, the inflow unit 110 engaged to the ringer spike 300 is moved together with the ringer spike 300 so that the first inflow hole 116 is moved to the inside of the securing unit 120. In addition, the bottom of the inflow unit 110 is retained by the retaining protrusion 142b so that the inflow unit 110 can be stably secured, but not continue to be moved in the movement direction of the ringer spike 300.

Thus, the introduction of the aqueous solution of the aqueous-solution pack 200 into the cover unit 130 is blocked, but not moved to the inside of the inflow unit 110 so that although the ringer spike 300 is separated from the infusion port 100, the aqueous solution of the aqueous-solution pack 200 does not flow out of the infusion port 100 any more.

In the meantime, although not shown, the infusion port 100 may be constructed such that the first movement-preventing step 114a is formed only at the lower portion of the first side surface 114 of the inflow unit 110 or the first retaining step 126 is formed only at the bottom of the securing unit 120 so that the securing unit 120 can secure the inflow unit 110 upon the insertion and withdrawal of the ringer spike 300.

As described above, according to the present invention, when the ringer spike 300 is inserted into the inflow unit 110, the top of the inflow unit 110 is moved to the inside of the cover unit 130 through the movement hole 122 of the securing unit 120 so that the aqueous solution of the aqueous-solution pack 200 introduced into the inflow unit 110 through the first inflow hole 116 can flow into the aqueous solution-introducing hole 310 of the ringer spike 300 and then can be administered to a body of the patient.

Moreover, when the ringer spike 300 is moved in the direction opposite to the aqueous-solution pack 200 so as to withdraw the ringer spike 300 from the infusion port 100, the inflow unit 110 engaged with the ringer spike 300 is moved together with the ringer spike 300 and simultaneously the first inflow hole 116 of the inflow unit 110 is moved to the inside of the securing unit 120. Thus, the introduction of the aqueous solution of the aqueous-solution pack 200 into the inflow unit 110 can be interrupted.

Figure 4:
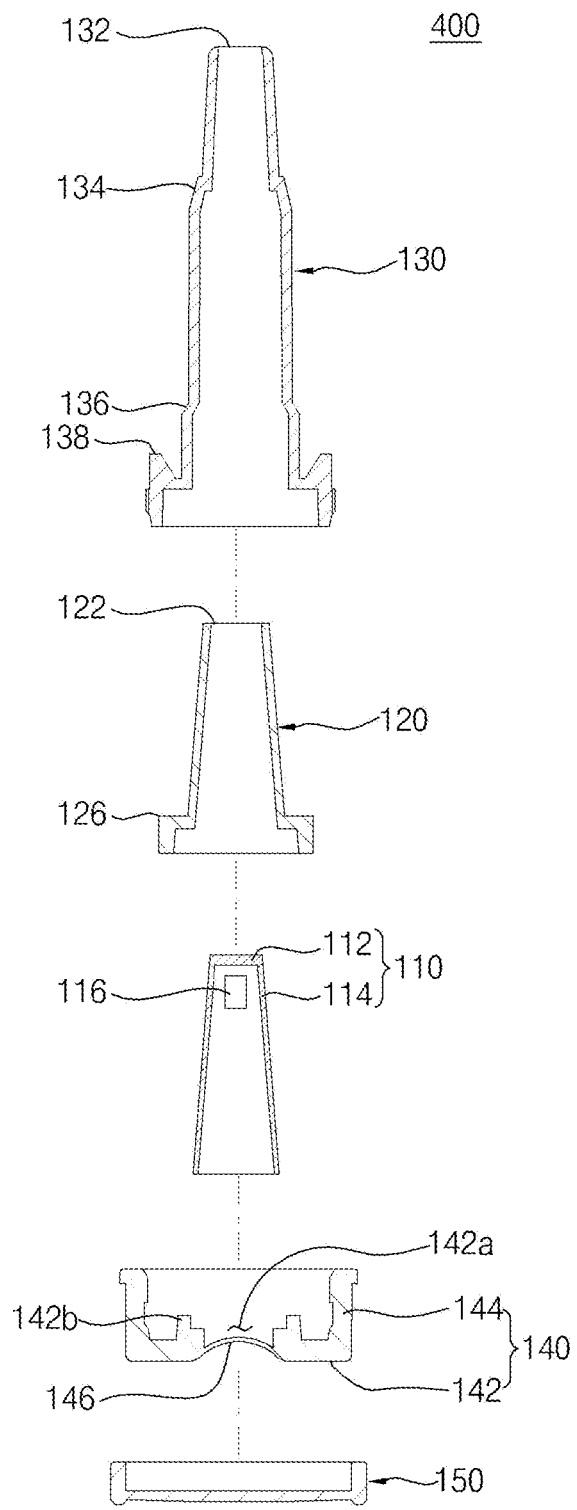
FIG. 4 is an exploded cross-sectional view illustrating an infusion port according to another embodiment of the present invention.

FIG. 4 is an exploded cross-sectional view illustrating an infusion port according to another embodiment of the present invention.

The infusion port according to this embodiment is substantially the same as that shown in FIG. 1 except a part of the inflow unit and a part of the securing unit. Thus, in this embodiment, the same elements as those described in the above embodiment of FIG. 1 are designated by the same reference numerals, and thus the repeated description thereof will be omitted to avoid redundancy.

Referring to FIG. 4, in the infusion port 400 according to another embodiment of the present invention, the first side surface 114 of the inflow unit 110 may include a first inclined part which is formed inclinedly so as to be gradually increased in diameter as it goes toward the bottom from the top surface 112 thereof so as to be firmly inserted into the inlet port 210. In addition, the outer surface of the securing unit 120 may include a second inclined part that is formed inclinedly so as to be gradually increased in diameter as it goes toward the first retaining step 126 from the movement hole 122 thereof so as to be firmly inserted into the inlet port 210.

In the case where the inflow unit 110 is moved to the outside of the securing unit 120 through the movement hole 122, since the bottom of the inflow unit 110 is larger in diameter than the top of the inflow unit 110, it can be secured stably without being moved to the outside of the securing unit 120. At this time, preferably, the diameter of the top surface 112 of the inflow unit 110 and an upper portion of the inflow unit 110 is smaller than that of the movement hole 122 of the securing unit 120 so that the upper portion of the inflow unit 110 is easily moved to the outside of the securing unit 120 through the movement hole 122. In addition, since the diameter of the bottom of the inflow unit 110 is larger than that of the movement hole 122, the bottom of the inflow unit 110 is prevented from being moved to the inside of the cover unit 130 through the movement hole 122.

Although not shown, the infusion port 400 may be constructed such that the first inclined part is formed only at a part of the first side surface 114 of the inflow unit 110 or the second inclined part is formed only at a part of the outer surface of the securing unit 120 so that the securing unit 120 can secure the inflow unit 110 upon the insertion and withdrawal of the ringer spike 300. Alternatively, the first inclined part is formed only on the first side surface 114 of the inflow unit 110 or the second inclined part is formed only on the outer surface of the securing unit 120.

While the infusion port according to the present invention has been described and illustrated in connection with specific exemplary embodiments with reference to the accompanying drawings, the present invention is not limited to the construction and operation described and illustrated herein. Therefore, since it will be readily appreciated by those skilled in the art that various modifications and changes can be made to the embodiments without departing from the technical spirit and scope of the present invention disclosed in the appended claims, the aforementioned description and the accompanying drawings should be construed to be merely illustrative of the present invention, but not to limit the technical spirit of the present invention.

The invention claimed is:

1. An infusion port regulating the inflow of an aqueous solution of an aqueous-solution pack into an external ringer spike as at least part of the ringer spike is inserted into or withdrawn from the infusion port, the infusion port comprising:
   an inflow unit configured to allow the ringer spike to be inserted thereto and having at least one first inflow hole formed thereon so as to allow for the inflow of the aqueous solution of the aqueous-solution pack as the ringer spike is inserted into the infusion port;
   a securing unit configured to surround at least part of the inflow unit and having a movement hole formed at one end thereof such that the first inflow hole of the inflow unit is moved to an outside or an inside of the securing unit as the ringer spike is inserted into or withdrawn from the infusion port, respectively, and configured to secure the inflow unit when the first inflow hole is moved to the outside of the securing unit; and
   a cover unit configured to house a securing part therein and having a second inflow hole formed at one end so as to allow for the inflow of the aqueous solution into the cover unit through the second inflow hole upon the partial insertion of the cover unit into an inlet port disposed at the aqueous-solution pack,
   wherein at least one of the securing unit and the inflow unit comprises a stepped part formed thereon so as to allow the securing unit to secure the inflow unit upon the insertion of the ringer spike thereto.

2. The infusion port according to claim 1, further comprising a securing cap configured to be engaged to the cover unit so that the securing cap fixes the inflow unit upon the withdrawal of the ringer spike from the infusion port, and having a central hole formed on one side thereof so as to allow for the insertion and withdrawal of the ringer spike into and from the securing cap through the central hole.

3. The infusion port according to claim 1, further comprising a contamination preventive cap configured to be engaged to a securing cap so as to prevent a central hole of the securing cap from being exposed to an outside.

4. The infusion port according to claim 1, wherein a securing cap comprises a barrier membrane configured to cover a central hole of the securing cap and formed of a flexible material to allow for the insertion and withdrawal of the ringer spike into and from the securing cap through the barrier membrane.

5. The infusion port according to claim 1, wherein a securing cap comprises a retaining protrusion formed along a circumference of the central hole thereof, and the securing unit comprises a first retaining step formed at a lower end thereof so as to be engaged with the retaining protrusion of the securing cap.

6. The infusion port according to claim 1, wherein the cover unit comprises a second retaining step formed at a lower end thereof so as to be engaged with a first retaining step of the securing unit.

7. The infusion port according to claim 1, wherein at least one of the securing unit and the inflow unit comprises a first inclined part formed thereon so as to allow the securing unit to secure the inflow unit upon the insertion of the ringer spike thereto.

8. The infusion port according to claim 1, wherein the inflow unit has a predetermined coefficient of elasticity to allow the ringer spike to be firmly inserted into the inflow unit upon the insertion of the at least part of the ringer spike thereto.

* * * * *